United States Patent
Linker et al.

(10) Patent No.: US 6,345,545 B1
(45) Date of Patent: Feb. 12, 2002

(54) TWO-STAGE PRECONCENTRATOR FOR VAPOR/PARTICLE DETECTION

(75) Inventors: Kevin L. Linker, Albuquerque; Charles A. Brusseau, Tijeras, both of NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/594,215

(22) Filed: Jun. 14, 2000

(51) Int. Cl.[7] .............................................. G01N 1/00
(52) U.S. Cl. .................................................. 73/863.23
(58) Field of Search ..................... 73/863.12, 863.21, 73/863.23, 864.71, 31.07, 28.04, 864.81; 96/413, 108, 122, 126, 129, 131, 132, 134, 135; 55/315, 315.1, 342, 342.1, 482, 482.1

(56) References Cited

U.S. PATENT DOCUMENTS 5,092,219 A * 3/1992 Roundbehler et al. ... 73/863.12
5,854,431 A   12/1998 Preconcentrator ........ 73/863.23

OTHER PUBLICATIONS

Artx Stainless Steel Vortex Tubes, 1 page, No date.
Artx Stainless Steel Air Guns, 1 page, No date.
Air Saver High–Thrust Jets, 1 page, No date.
Hannum, Parmeter, Linker, Rhykerd & Varley, Miniaturized Explosive Preconcentrator for Use in a Man–Portable Field Detection System, No date.

* cited by examiner

*Primary Examiner*—Robert Raevis
(74) *Attorney, Agent, or Firm*—George H. Libman

(57) ABSTRACT

A device for concentrating particles from a high volume gas stream and delivering the particles for detection in a low volume gas stream includes first and second preconcentrators. The first preconcentrator has a first structure for retaining particles in a first gas flow path through which a first gas flows at a relatively high volume, valves for selectively stopping the first gas flow; and a second gas flow path through which gas flows at an intermediate flow volume for moving particles from the first structure. The second preconcentrator includes a second structure for retaining particles in the second gas flow path; a valve for selectively stopping the second gas flow; and a third gas flow path through which gas flows at a low volume for moving particles from the second structure to a detector. Each of the particle retaining structures is preferably a metal screen that may be resistively heated by application of an electric potential to release the particles.

23 Claims, 3 Drawing Sheets

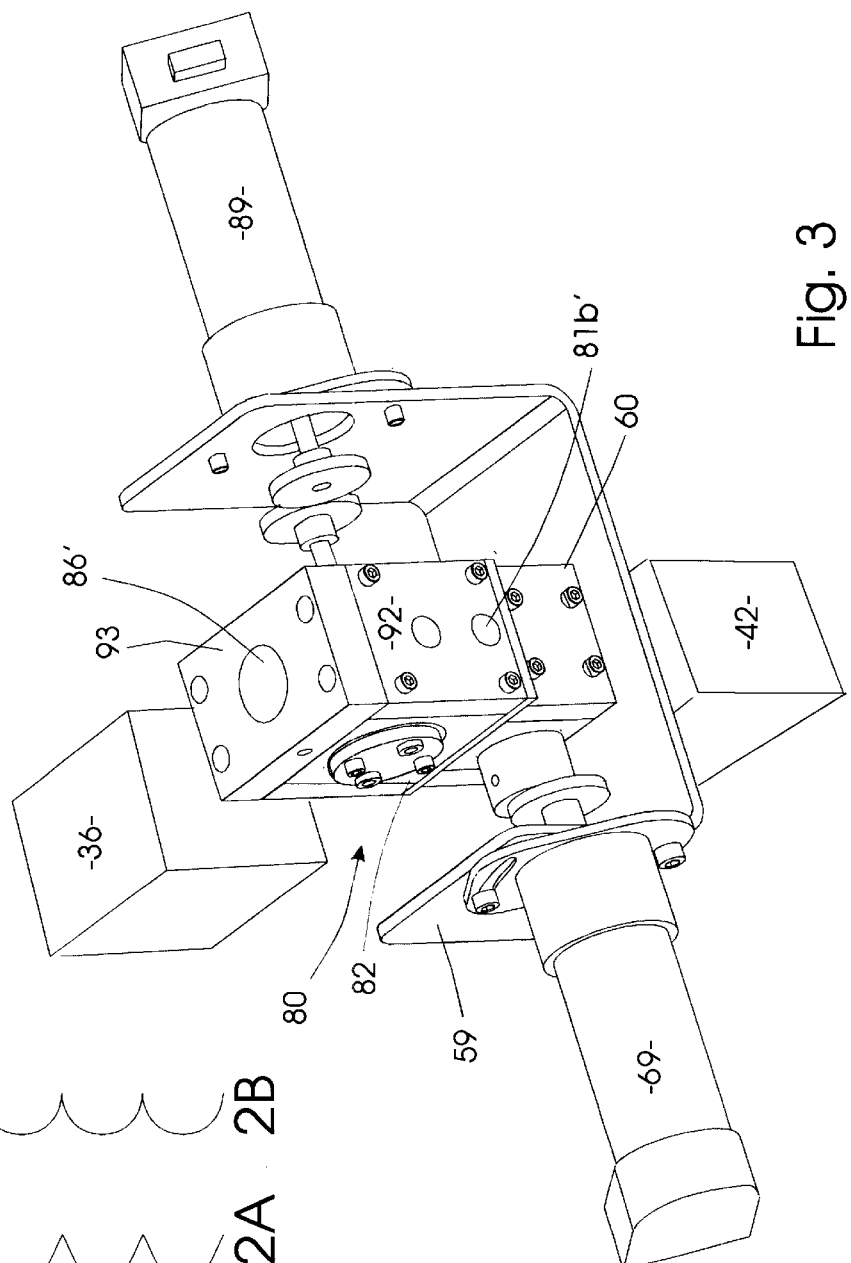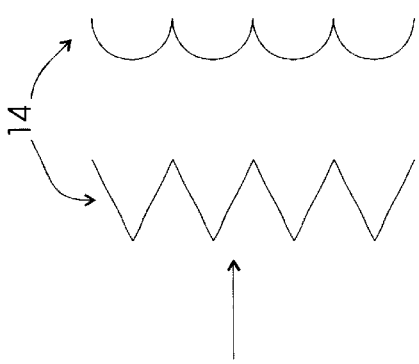

TWO-STAGE PRECONCENTRATOR FOR VAPOR/PARTICLE DETECTION

The United States Government has rights in this invention pursuant to Department of Energy Contract No. DE-AC04-94AL85000 with Sandia Corporation.

CROSS REFERENCE TO RELATED APPLICATIONS (Not Applicable)

BACKGROUND OF THE INVENTION

Trace chemical detection of explosives, i.e., the art of detecting explosive materials from minute quantities of vapor and/or microscopic particles (hereinafter referred to as 'particles'), can be an important aspect of many physical security systems. Among the challenges currently confronting researchers in this area is the problem of how to collect the explosive sample and transport it to the detector without major losses. In many applications, especially applications involving the general public such as airport passenger screening, swipe collection of particles via direct physical contact with the person or object to be screened for explosives is either too physically invasive or time consuming, so it is necessary to base the collection process on air flows. But the vapor and/or airborne particle material that is collected in such air flows is usually far more dilute than the detector is capable of measuring, and the air flow is often too large to be directly accommodated by the detector. These disparities give rise to preconcentrators, devices which take a trace sample of a material from a large incoming air flow and concentrate the material into a smaller volume before it is introduced into a trace detector.

U.S. Pat. No. 5,854,431 of Linker et al discloses a single stage preconcentrator 10 for use in collecting particles from an air stream that passes over a person or object under observation. Preconcentrator 10 includes a screen 14 disposed between input and output air stream valves 22 and 22', respectively, which valves are secured together to form a layered arrangement whereby gas to be tested passes through open valve 22, through screen 14 (where particles are deposited), and exits through open valve 22'. A fan or other gas moving device may be situated downstream of output valve 22', and the source upstream of input valve 22 may be the output of a booth through which people or objects being tested may pass.

As set forth in the '431 patent, screen 14 is preferably formed of a metallic felt made from very thin metal filaments, with diameters ranging from 1 to 80 micron. As a comparison, human hair has a diameter between 70 and 100 micron. The felt is a pleatable and weldable stainless steel matrix, produced by the sintering of a composite metal fiber. The preferred material is Bekipor® ST, produced in North Carolina by Bekaert Fibre Technologies of Belgium. The preferred configuration of screen 14 was pleated, with the folds being parallel to the flow of gas during desorption. A particular advantage of this screen material is that it may be resistively heated to release the particles from the surface by applying an electric potential across its surface.

Single stage preconcentrator 10 of the '431 patent operates as follows: first—both valves 22, 22' are open and air to be tested flows through screen 14, which is not being heated and which absorbs particles from the air to be tested; second—both valves 22, 22' are closed and screen 14 is heated to desorb collected particles; and third—a carrier gas 34 (air or inert gas) is provided to move desorbed particles in a direction parallel to the pleated surface of screen 14 to a detector at output 40.

A problem with this device is that the output 40 flows at about 4 liters/minute in order to move the particles from screen 14, while the detector prefers an input on the order of 0.1 to 0.5 liters/minute.

Simple flow restrictors would not work in this application, because the particles may adsorb to the restrictor instead of proceeding to the detector. In addition, any solution to this problem must be capable of being reset after every test so that the results of the previous test do not effect the next test.

SUMMARY OF THE INVENTION

It is an object of this invention to provide a 2-stage preconcentrator to enable particles to be moved to a detector under conditions acceptable to the detector, and to provide for cleaning of one stage while the other stage is operating.

To achieve the foregoing and other objects, and in accordance with the purpose of the present invention, as embodied and broadly described herein, the present invention may comprise a device for concentrating particles in a high volume gas flow for detection in a low volume gas comprising a first preconcentrator comprising a first structure for retaining particles in a first gas flow path through which a first gas flows at a relatively high flow; means for selectively stopping the first gas flow; and a second gas flow path through which gas flows at an intermediate flow for moving the particles from the first structure to a second preconcentrator coupled to said first preconcentrator. The second preconcentrator comprises a second structure for retaining particles in the second gas flow path; means for selectively stopping the second gas flow; and a third gas flow path through which gas flows at a relatively low rate for moving the particles from the second structure to a detector.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

FIGS. 2A and 2B show an end view of the previous and present configurations of first preconcentrator screen.

FIG. 3 shows a perspective view of the second stage of the invention.

DETAILED DESCRIPTION OF THE INVENTION

Figure 1:
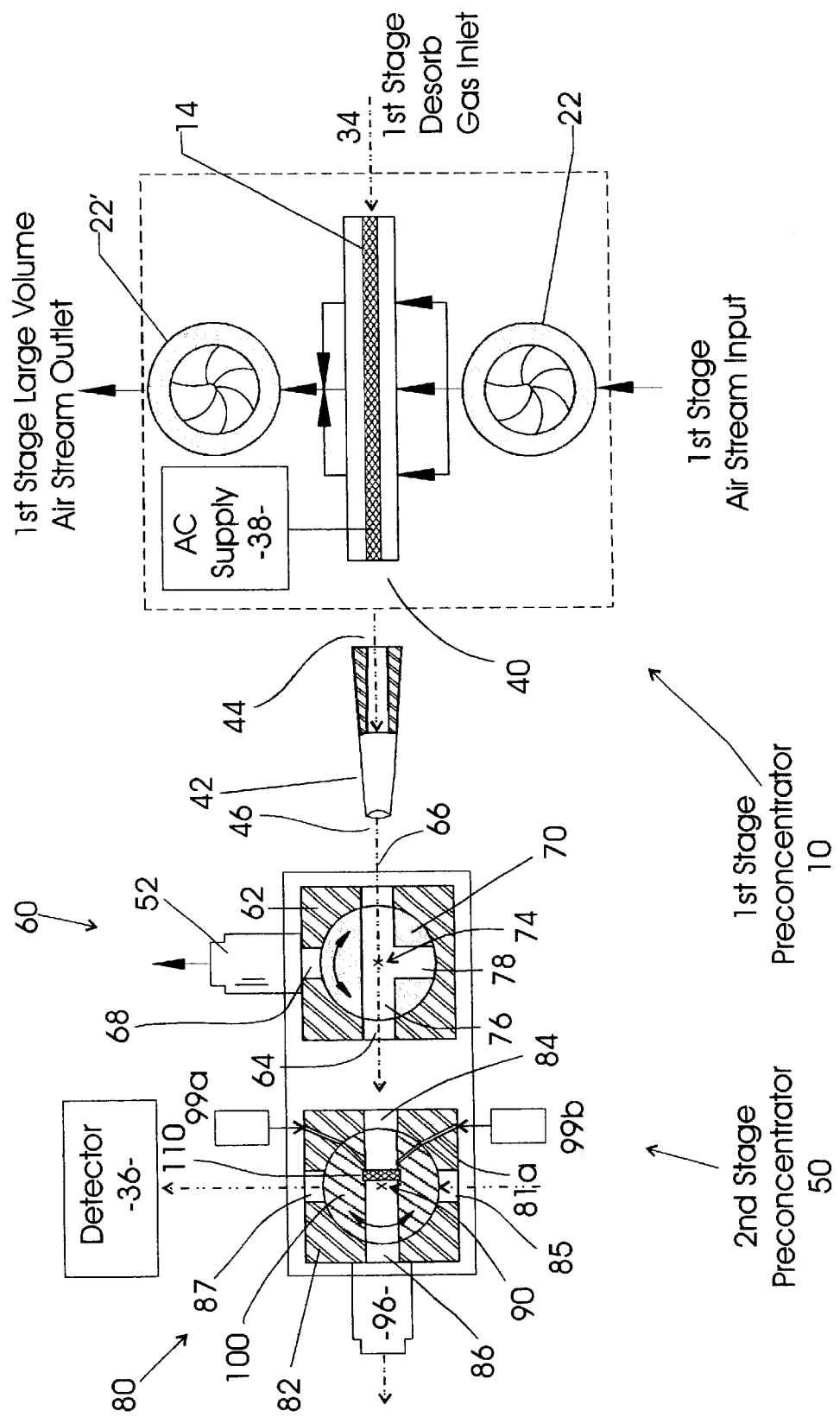
FIG. 1 shows a schematic representation of the invention.

As shown in FIG. 1, a two-stage preconcentrator for detection of particles in a gas stream may include a first stage preconcentrator 10 and a connected second stage preconcentrator 50. A preferred embodiment of first stage preconcentrator 10 is disclosed in U.S. Pat. No. 5,854,431, the disclosure of which patent is incorporated herein by reference. As discussed in the aforementioned '431 patent, a first gas flow is through flow control means such as air stream valves 22, 22' and screen 14 may be multi-bladed irises similar to a camera shutter. However, since 6" diameter shutters of this type are not readily available, valves 22, 22' may also be single leaf shutters that cover a hole and pivot about a point adjacent the outer perimeter of the hole. Tests have shown that valves 22, 22' do not have to be well sealed against leaks to permit the invention to function as designed; in fact, for reasons that are not totally understood, shutters that were very well sealed against leaks did not perform as well as less well-sealed shutters.

The '431 patent used a pleated screen 14 with a zig-zag cross-section as shown in cross-section in FIG. 2A, with pleat height being about ½ inch and the distance between peaks being about ¼ inch in a 6"×6" screen; the invention uses a scalloped screen 14 with a cross-section as shown in FIG. 2B wherein every other pleat is rounded, with a pleat height of about ⅜ inch and distance between peaks of about ¾ inch. The configuration of FIG. 2B has been found to give improved performance over the configuration of FIG. 2A during desorption of particles after collection. It is believed this improved performance results from fewer particles being caught in the valley between adjacent pleats.

As seen in the '431 patent, the output 40 of first stage preconcentrator is a slot that is approximately the same dimension as the edge dimensions of screen 14 (approximately 6"×0.5"). The output 40 is fed into a funnel 42 that has a similarly shaped input 44 and a round smaller output 46 connected to the input of a second stage preconcentrator 50.

Second stage preconcentrator 50 captures the particles from screen 14 of first stage preconcentrator 10 and pass them to a detector at a lower flow rate with minimal loss of particles. Second stage preconcentrator 50 preferably comprises an input stage 60 connected in series with an output stage 80. As shown in FIG. 3, input stage 60 is adjacent and attached to output stage 80, and both stages are held by a bracket 59. A motor 69 is attached to one side of bracket 59 and drives, through appropriate gears, a rotating valve 70 in input stage 60 as discussed hereinafter. A second motor 89 is also attached to bracket 59 and drives, through other gears, a rotating valve 100 in output stage 80 as discussed hereinafter.

One embodiment of input stage 60 includes a solid rectangular housing 62 having a cylindrical bore extending between two opposed faces. Rotary valve 70 is formed of a solid cylinder of a material such as stainless steel having a diameter sized to fit tightly within the bore of housing 62. (As illustrated, the axis 74 of valve 70 extends into the page in FIG. 1 and extends parallel to the axis of motor 69 in FIG. 3) Valve 70 includes a first hole 76 extending in a straight line perpendicular to axis 74 and through valve 70, and a second hole 78 extending perpendicular to and from hole 76 at axis 74 to the surface of valve 70. A hole 66 through a side of housing 62 provides an input for input stage 60 enabling gas from first stage preconcentrator 10 to communicate with valve 70. Another hole 64 through an opposing side of housing 62 provides an output from input stage 60 enabling gas passing through valve 70 to communicate with output stage 80.

Holes 66 and 64 are preferably aligned so they and first hole 76 of valve 70 provide a clear, straight gas path from first stage preconcentrator 10 to output stage 80 when valve 70 is in the position shown in FIG. 1. This position is referred to as the 90° C. position of input stage 60.

A third hole 68 through housing 62 enables valve 70 to communicate with a thrust jet 52. (According to literature of the manufacturer, Artx Ltd of Cincinnati, Ohio, thrust jet 52 is a tubular device that releases a tiny amount of compressed air at near-sonic velocity through an internal ring-shaped nozzle. The high-speed 'tube' of air ejected through the front of the device creates a strong vacuum which pulls additional surrounding air through the rear of the device.)

If valve 70 is rotated 90° C. counter-clockwise from the position shown in FIG. 1, housing hole 66 is aligned with cylinder hole 78 and housing hole 68 is aligned with cylinder hole 76, enabling gas to flow between housing holes 66 and 68. This position is referred to as the 180° C. position of input stage 60.

If valve 70 is rotated 90° C. clockwise from the position shown in FIG. 1, housing hole 64 is aligned with cylinder hole 78 and housing hole 68 is aligned with cylinder hole 76, enabling gas to flow between housing holes 64 and 68. This position is referred to as the 0° C. position of input stage 60.

Figure 4:
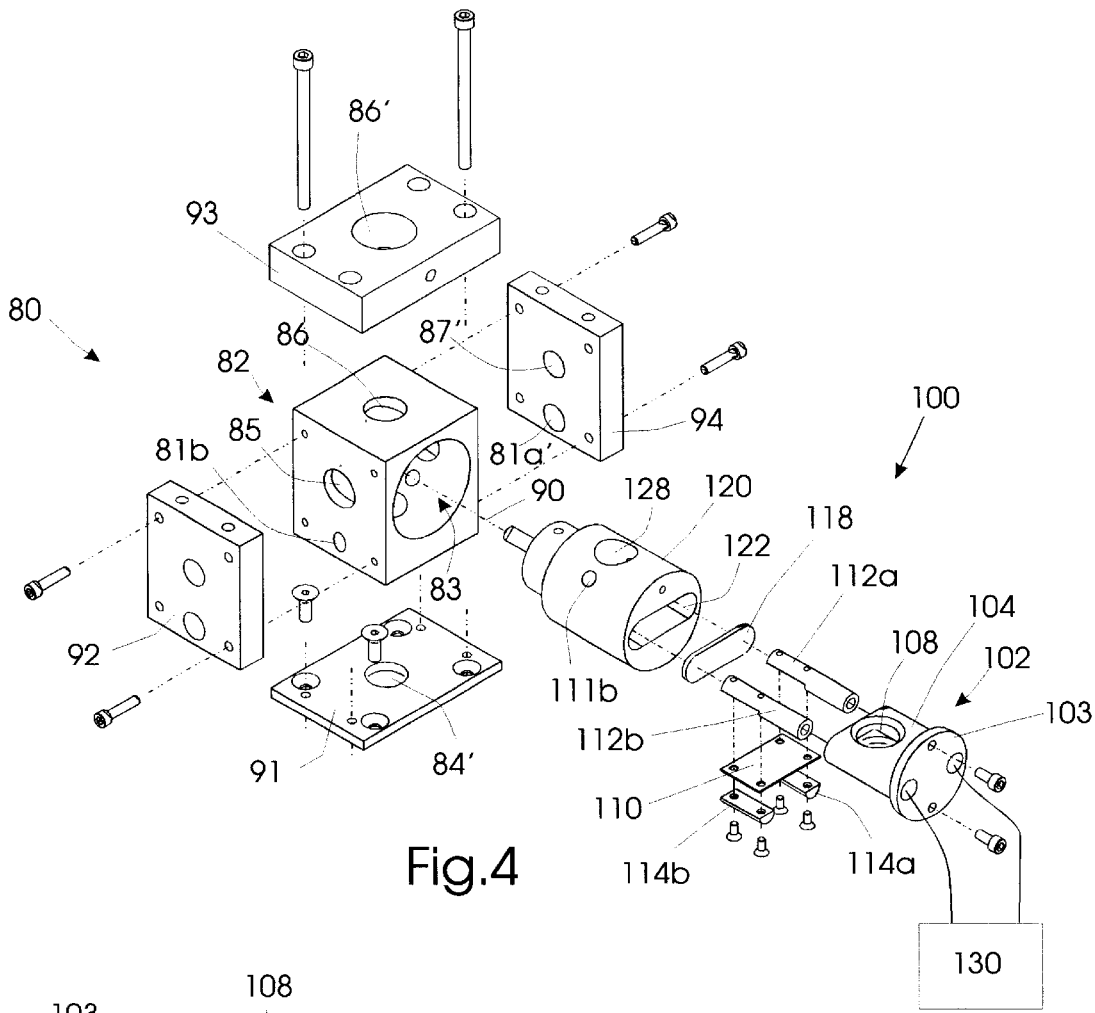
FIG. 4 shows an exploded view of the output stage of the second stage.

Output stage 80 of second stage preconcentrator 60 is shown in FIGS. 1 and 4 to include a second particle collecting screen 110, preferably flat and made of the same metal fiber felt material as screen 14 in the first stage preconcentrator 10. Screen 110 is mounted on, and electrically insulated from, valve 100 that rotates within a housing 82. Means are provided to heat screen 110 to desorb particles, as discussed hereinafter.

Each of housings 62 and 82 are preferably made of a material to which particles being detected do not readily adhere. Teflon® is a good particle-resistant material for systems designed to detect explosive particles. However, because it is difficult to make mechanical attachments to Teflon®, each housing is preferably surrounded by aluminum plates through which suitable holes are bored to facilitate attachment to neighboring elements of the invention.

As shown in FIG. 4, housing 82 is preferably a regular parallelogram (such as a cube) with a central bore 83 that receives valve 100. The four surfaces that surround bore 83 are covered by aluminum plates 91–94. Each plate has holes which align with the holes in the surface of housing 82, such as 86 and 86'. For most of the discussion of this embodiment of the invention, hole 86 should be understood to mean the hole through both plate 93 and housing 82, and the surface 93 of housing 82 should be understood to mean the surface of plate 93.

Alternatively, housings 62 and 82 and parts of valve 100 could be manufactured from aluminum or other material, and the surfaces which are exposed to particles could be coated with Teflon® or other particle-resistant material such as ceramic.

Housing 82 has a plurality of gas passage holes arranged perpendicular to the axis 90 of valve 100. An input port 84 and an aligned third port 86 extend through one pair of opposite surfaces 91, 93 of housing 82, and a fourth port 85 and an aligned output port 87 extend through the other pair of opposite surfaces 92, 94 of housing 82. A thrust jet 96 (FIG. 1) is attached to third port 86, and input port 84 is coupled with output port 64 of input stage 60. The detection device 36 is connected to output port 87.

Housing 82 also includes another pair of holes 81a, 81b for directing cooling air to the screen 110 through valve body 120 via holes 111a and 111b. Vortex coolers 99a, 99b are connected to each of holes 81a, 81b (FIGS. 1, 4), which holes are formed so that their ends inside valve body 120 are adjacent to the input side of screen 110 when valve 100 is in the position shown in FIG. 1. (Vortex coolers have been known since the 1930s and are available from ARTX Ltd, among other sources. A vortex cooler consists of a hollow tube which has a side opening for compressed air. Due to the construction of the tube, heated air comes out of one end and cooled air comes out of the other end of the hollow tube.)

Figure 5:
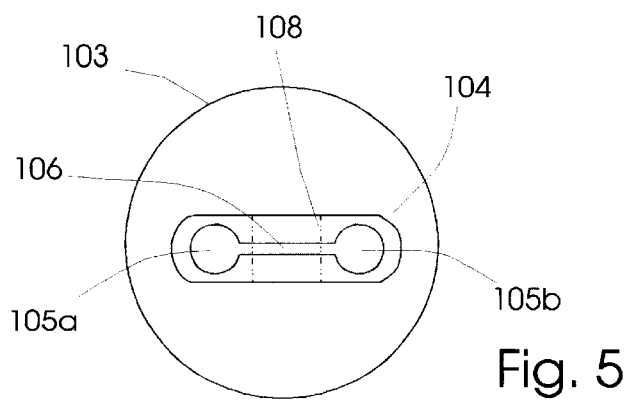
FIG. 5 shows an end view of a portion of the output stage.

Valve 100 is shown in FIGS. 4 and 5 to include a plurality of parts. An electrically conducting assembly includes rectangular screen 110, which is affixed at each end to a different one of a pair of spaced electrically conducting rods 112a, 112b. Each rod 112a, 112b is split in half lengthwise from an end a distance corresponding to the width of screen 110. The half-cylindrical split pieces 114a, 114b are then fastened back into their original place with the screen between that piece and the other half of the rod, as shown in FIGS. 4 and 5. This assembly is held by an electrically insulating, particle-resistant, holder 102 (preferably Teflon® or high-temperature ceramic) that includes an end cap 103 and a generally rectangular slab 104 extending from end cap 103. As shown in FIG. 5, a pair of spaced holes 105a, 105b extend into slab 104 from the end opposite end cap 103, and a slot 106 extends between holes 105a, 105b. These pieces are sized such that rod 112a slides into hole 105a, rod 112b slides into hole 105b, and screen 110 slides into slot 106. A hole 108 extending through slab 104 permits gas to flow through screen 110. An electrical power supply 130 (1.5 v AC) is connected through holes in end cap 103 to the ends of rods 112a, 112b to apply a voltage across screen 110.

Valve 100 further comprises a generally cylindrical stainless steel body 120 that is sized to fit into bore 83 in housing 82. A generally rectangular slot 122 is cut into body 120 from one end thereof for holding slab 104 and the electrically conducting assembly discussed above. A hole 128 extends through body 120 and communicates with hole 108 in slab 104. A pair of holes 111a, 111b in body 120 complete the passages 81a, 81b between vortex coolers 99a, 99b and screen 110 when valve 100 is in the position shown in FIG. 1. An insulating spacer 118 is placed between the exposed ends of rods 112a, 112b and the interior of valve body 120.

Motor 89 (FIG. 3) rotates valve 100 to any of three positions. As shown in FIG. 1, valve 100 is in the 0° C. position with the input side of screen 110 facing input hole 84 and holes 111a, 111b aligned with passages 81a, 81b in housing 82. If valve 100 is rotated 180° C. to face hole 86, it is in the 180° C. position. If it is rotated 90° C. counterclockwise from the position shown in FIG. 1 to face hole 87, it is in the 90° C. position.

The operation of the invention involves several process steps as outlined below:

1. First Stage Adsorb From Source

Valve 70 is placed in the 0° C. position to block gas flow through hole 66 and to permit flow between holes 64 and 68 when the second stage is cleaned. Valves 22, 22' are open, and a large volume of air or other gas flows from the source to be tested through valves 22, screen 14, and out through valve 22'. The heater for the first stage is off, as particles in the gas stream adsorb to a cool screen more than a hot screen. Explosive particles from the gas flow impinge on and adsorb to cool felt screen 114.

2. Clean Second Stage

This step may occur simultaneously with step 1. Valve 100 is placed in the 180° C. position with the screen facing hole 86. Voltage from supply 130 is applied to heat screen 110 to desorb any remaining particles. Thrust jet 96 is activated to create a flow through screen 110. Input gas passes from input stage 60 (through thrust jet 52 (which is off), hole 68, valve 70, and hole 64) to output stage 80 (through hole 84, hole 128, hole 108, screen 110, hole 108, hole 128, and hole 86) to be exhausted by thrust jet 96.

3. End First Stage Adsorb From Source

The source of air from the object under test is stopped and valves 22, 22' are closed.

4. Desorb Particles From The First Stage 10 To The Second Stage 50

The second stage heater 130 is turned off and the first stage heater 38 is turned on. In input stage 60, valve 70 is rotated to the 90° C. position and valve 100 is rotated to the 0° C. position (the position of the valves shown in FIG. 1). Thrust jet 96 is turned on to draw gas with particles from first stage 10, through funnel 42, input stage 60 and through screen 110 in output stage 80. The gas and particles from screen 14 are quite warm (over 140° C.) when they reach output stage 80 as a result of heating of screen 14. This heat, and the relatively high flow rate, keeps particles from adsorbing to the aluminum funnel 42. Since warm particles will not adsorb to screen 110, vortex coolers 99a and 99b are turned on to provide a flow of cold air that cools the particles and screen 110.

5. Particle Detection

Thrust jet 96 and vortex coolers 99a, 99b are turned off. Valve 100 is rotated counterclockwise to the 90° C. position so that screen 110 faces the detector and gas flow through holes 84 and 86 is blocked. Heater 130 for screen 110 is energized to desorb the trapped particles. The detector generates a low volume gas flow towards the detector to cause particles to be carried from the screen 110 through hole 87 to the detector. Opposing hole 85 provides the input for this flow.

6. Clean First Stage

This step may occur simultaneously with step 5. Valve 70 is rotated to the 180° C. position and power supply 38 is energized to heat screen 14. Thrust jet 52 is turned on to draw air from inlet 34 over screen 14, through hole 66 to hole 68.

With two stage preconcentration the demonstrated sensitivity of the system has increased by at least an order of magnitude over the single stage preconcentrator of the '431 patent, from low nanograms ($10^{-9}$) to high picograms ($10^{-12}$). This increase in sensitivity provides a significant increase in the capability of a portal system using the preconcentrator to detect explosives on people passing through the portal.

The particular sizes and equipment discussed above are cited merely to illustrate a particular embodiment of this invention. It is contemplated that the use of the invention may involve components having different sizes and shapes as long as the principle of using two preconcentrator stages, is followed. For example, the sizes of openings, screens, and gas flow may be adjusted to meet requirements of an application.

Although aluminum has been utilized for many of the metal parts of this invention, it should be understood that these parts may also be formed of stainless steel or other materials that are less attractive to explosive or other particles being detected. Particles have not been observed to stick to aluminum funnel 42 because of the relatively high air flow. If particles did adsorb to funnel 42, it could be made of a more particle-resistant material, or means such as an additional air source or holes could be provided in funnel 42 to provide a flow of air along the inside edges that keep particles towards the center of funnel 42.

Detector 36 is preferably an ion mobility spectrometer, a time-of-flight mass spectrometer, and other known device for measuring mass and time of flight.

In addition, alternative materials or structures may be utilized for screens 14 and 110. Any screen or surface that has the desired properties of retaining particles (for steps 1 and 4) until they are controllably released (for steps 2, 4, and 6) may be utilized in place of screens 14 and 110. It is intended that the scope of the invention be defined by the claims appended hereto.

What is claimed is:

1. A device for concentrating particles in a high volume gas stream for delivery in a low volume gas stream to a detector, comprising:

a first preconcentrator comprising:

a first structure for retaining particles in a first gas flow path through which a first gas flows at a high flow rate and volume;

means for selectively stopping said first gas flow; and a second gas flow path through which gas flows at an intermediate flow for moving said particles from said first structure; and a second preconcentrator coupled to said first preconcentrator, said second preconcentrator comprising:

an input stage having an input housing including:

an input port connected to said second gas flow path, an output port, and a third port; and a valve having a first position where said input port is connected only to said output port, a second position where said input port is connected only to said third port; and a third position where said third port is connected only to said output port; and an output stage having an output housing including:

and input port connected to said output port of said input stage; and output port; a third port and a fourth port; and a valve having a valve gas flow path extending only from a valve input, through porous particle collecting structure, to a valve output; said valve having a first position where said valve input is only connected to said input and said output is only connected to said third port; a second position where said valve input is only connected to said output port and said valve output is only connected to said fourth port; and a third position where said valve input is connected only to said third port and said valve output is connected only to said input port.

2. The device of claim 1 wherein said first structure is a first electrically conductive metal screen.

3. The device of claim 2 wherein said first gas flow path flows through said first screen, wherein particles in said gas flow are caught by said first screen.

4. The device of claim 3 further comprising means for heating said first screen to release said particles from said first screen.

5. The device of claim 4 wherein said means for heating consists of an electric potential applied to resistively heat said first screen.

6. The device of claim 3 wherein said second gas flow path is across said first screen and across said first gas flow path.

7. The device of claim 6 wherein said first screen is a sheet of material that has a plurality of parallel pleats extending parallel to said second gas flow path.

8. The device of claim 7 wherein every other pleat is rounded so that a cross-section of said sheet forms a series of parallel half domes.

9. The device of claim 1 wherein said valve gas flow path is straight.

10. The device of claim 9, further comprising a first means for controllably pulling gas from said third port of said input stage and a second means for controllably pulling gas from said third port of said output stage.

11. The device of claim 10 wherein said first means and said second means for controllably pulling gas each comprise a thrust jet connected to one of said third ports.

12. A device for concentrating particles in a high volume gas stream for delivery in a low volume gas stream to a detector, comprising:

a first preconcentrator comprising:

an electrically conductive metal screen for retaining particles in a first gas flow path through which a first gas flows at a high flow rate and volume,wherein particles in said gas flow are caught by said first screen;

means for selectively stopping said first gas flow; and a second gas flow path across said first screen and across said first gas flow path through which gas flows at an intermediate flow for moving said particles from said first structure, wherein said first screen is a sheet of material that has a plurality of parallel pleats extending parallel to said second gas flow path, every other pleat being rounded so that a cross-section of said sheet forms a series of parallel half domes; and a second preconcentrator coupled to said first preconcentrator, said second preconcentrator comprising:

a second structure for retaining particles in said second gas flow path;

means for selectively stopping said second gas flow; and a third gas flow path through which gas flows at a relatively low rate for moving said particles from said second structure to a detector.

13. The device of claim 1 further comprising means for controllably heating said porous particle collecting structure.

14. The device of claim 13 wherein said porous particle collecting structure is electrically insulated from said valve, and said means for heating consists of an electric potential applied to resistively heat said structure.

15. The device of claim 1 further comprising an additional port in said output housing, a hole extending through said housing and said valve to a location adjacent said porous particle collecting structure only when said valve is in the first position; and a controllable source of cool air attached to said additional port.

16. The device of claim 15 wherein said source of cool air is a vortex cooler.

17. The device of claim 1 further comprising a particle detector connected to said output port.

18. A preconcentrator for concentrating particles in a gas flow path comprising:

an input stage having an input housing including:

an input port, an output port, and a third port; and an input stage valve having a first position where said input port is connected only to said output port, a second position where said input port is connected only to said third port; and a third position where said third port is connected only to said output port; and an output stage having an output housing including an input port connected to said output port of said input stage; an output port; a third port and a fourth port; and an output stage valve having a gas flow path extending only from a valve input, through porous particle collecting structure, to a valve output; said valve having a first position where said valve input is only connected to said input port and said valve output is only connected to said third port; a second position where said valve input is only connected to said output port and said valve output is only connected to said fourth port; and a third position where said valve input is connected only to said third port and said valve output is connected only to said input port.

19. The preconcentrator of claim 18 wherein said porous particle collecting structure comprises a flat metallic screen.

20. The preconcentrator of claim 9 wherein said valve comprises:

a cylindrical body having a straight hole defining part of said gas flow path extending through said body perpendicular to the axis of said body, said body also having a body slot extending into said body along the axis from one end; and a screen holder having a slab portion extending into said slot from an end portion, said slab portion having a through hole that aligns with said straight hole when said slab portion is placed in said slot, and a slab slot extending within said slot through said hole for holding said screen within said hole.

21. The preconcentrator of claim 20 wherein said slab slot extends from an end of said slab.

22. The preconcentrator of claim 21 wherein said screen holder is made of an electrically insulating material.

23. The preconcentrator of claim 22 wherein said electrically insulating material is one of the group consisting of Teflon® and high-temperature ceramic.

* * * * *

UNITED STATES PATENT AND TRADEMARK OFFICE
CERTIFICATE OF CORRECTION

PATENT NO.    : 6,345,545 B1
DATED         : February 12, 2002
INVENTOR(S)   : Kevin Linker et al.

It is certified that error appears in the above-identified patent and that said Letters Patent is hereby corrected as shown below:

<u>Column 9,</u>
Line 10, delete "9" and insert -- 19 -- and insert -- output stage -- before "valve".

Signed and Sealed this

First Day of April, 2003

JAMES E. ROGAN
*Director of the United States Patent and Trademark Office*